(12) United States Patent
Souvie et al.

(10) Patent No.: US 6,320,058 B2
(45) Date of Patent: Nov. 20, 2001

(54) PROCESS FOR THE PREPARATION OF ISOINDOLINE

(75) Inventors: Jean-Claude Souvie, Le Havre; Claude Fugier, Gruchet le Valasse; Jean-Pierre Lecouve, Le Havre, all of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/785,956

(22) Filed: Feb. 16, 2001

(30) Foreign Application Priority Data

Feb. 25, 2000 (FR) .................................................. 00 02383

(51) Int. Cl.⁷ .................................................. C07D 209/44
(52) U.S. Cl. ............................................. 548/470; 548/482
(58) Field of Search ..................... 548/482, 470

(56) References Cited

U.S. PATENT DOCUMENTS 2,773,902 * 12/1956 Heaton et al. ........................ 260/578

OTHER PUBLICATIONS

L. Kh. Freidlin et al., Formation of nitrogenous heterocycles in catalytic hydrogenation of dinitriles of succinic and phthalic acids. Izvest. Akad. Nauk S.S.S.R. Otdel. Khim. Nauk., 1959, pp. 1859–1862.*

P.N. Rylander, Catalytic Hydrogenation in Organic Syntheses, 1979, pp. 140–142; ISBN 0–12–605355–3.*

* cited by examiner

*Primary Examiner*—Mukund J. Shah
*Assistant Examiner*—U. Malhikarjunc Rao
(74) *Attorney, Agent, or Firm*—The Firm of Hueschen and Sage; G. Patrick Sage

(57) ABSTRACT

Process for the industrial synthesis of isoindoline by catalytic hydrogenation of phthalonitrile, and its application in the synthesis of 2-(S)-benzyl-4-oxo-4-(cis-perhydroisoindol-2-yl)-butyric acid, its pharmaceutically acceptable salts and its hydrates.

12 Claims, No Drawings

PROCESS FOR THE PREPARATION OF ISOINDOLINE

BACKGROUND OF THE INVENTION

Isoindoline is a synthesis intermediate that is widely used, especially in the preparation of pharmaceutical active ingredients.

In particular, isoindoline is an important intermediate in the synthesis of 2-(S)-benzyl-4-oxo-4-(cis-perhydroisoindol-2-yl)butyric acid of formula (I):

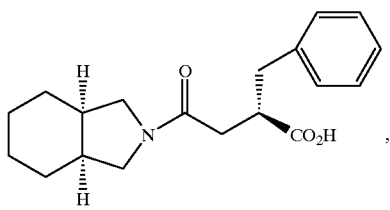

its pharmaceutically acceptable salts and its hydrates.

The compound of formula (I), and its addition salts and hydrates, have especially valuable pharmacological properties. They are very powerful insulin secretors, which makes them useful in the treatment of non-insulin-dependent diabetes. The compound of formula (I), its preparation and its therapeutic use have been described in Patent Specification EP 0 507 534. Its industrial preparation is described in Patent Specification WO 99/01430. Given the pharmaceutical value of this compound, it was important to be able to obtain the intermediate isoindoline using a high-performance industrial synthesis process.

DESCRIPTION OF THE PRIOR ART

A number of methods for the preparation of isoindoline are already known. No process described in the literature, however, enables isoindoline to be obtained with satisfactory purity and yield, whilst still being readily transposable to an industrial scale and advantageous from the point of view of profitability.

The preparation of isoindoline by the electrolytic or chemical reduction of phthalimide is described in the journals Bull. Soc. Chim. France 1956, 906–910, J. Pharm. Sci. 1964, 53(8), 981 and J. Org. Chem. 1988, 53 (22), 5381–5383.

Those processes do not, however, enable isoindoline to be obtained in a yield of more than 50%.

The preparation of isoindoline by cyclising α,α'-dibromo-xylene in the presence of p-toluenesulphonylamine, followed by deprotection of the resulting N-(p-toluenesulphonyl)-isoindoline is described in the journals J. Org. Chem. 1957, 22 , 1255–6 and Org. Synth. Collect. Vol. V, 406–408 and 1064–1066.

That method, in addition to its low yield (less than 50%), has the disadvantage of using a highly lacrimogenic starting material.

Patent Specifications FR 1 577 845 and FR 1 578 582 describe the preparation of isoindoline by reacting α,α'-dichlorobenzene with hexamethylenetetraamine, followed by treatment of the resulting ammonium salt in an HCI or $SO_2$ medium, and then cyclisation of the resulting o-chloromethyl-benzyl amine compound in a basic medium. That method is especially lengthy and does not enable isoindoline to be obtained with a satisfactory yield.

The journal Izvestia Eng. Ed. 1959, 1778–80, describes the synthesis of isoindoline by hydrogenation of phthalonitrile at 100–120 atm in a dioxane/ammonia mixture, in the presence of nickel or cobalt at 100° C.

That process has several disadvantages. It has not been possible to reproduce the stated yields (91 to 98%). After removal of the catalyst by filtration and removal of the solvent by distillation, it has not been possible to distill off any compound from the medium heated to 120° C. in vacuo at 20 mbars. Moreover, in the case of industrial-scale processing the presence of ammonia in the reaction mixture requires a special installation in order to protect the environment.

DETAILED DESCRIPTION OF THE INVENTION

Given the value of isoindoline as an intermediate in the synthesis of pharmaceutical active ingredients, especially 2-(S)-benzyl-4-oxo-4-(cis-perhydroisoindol-2-yl)-butyric acid, and given the absence of a process that enables it to be obtained with a good yield and satisfactory purity, starting from inexpensive starting materials but avoiding the use of ammonia, the Applicant carried out in-depth research, which resulted in the development of a new process for the preparation of isoindoline.

This process enables isoindoline to be obtained in a single step, by simple catalytic hydrogenation of phthalonitrile, a commercial product, without the addition of ammonia, with a yield of more than 75% and with very good purity.

In order to obtain that result, the following operating conditions must be applied:

The catalyst used is 5% Pt/C. In fact, it became apparent, surprisingly, that of all the catalysts generally employed, only Pt/C enabled isoindoline to be obtained within a reasonable reaction time (Table 1).

The amount of Pt/C used is from 10 to 25%, preferably 20%, of the weight of the phthalonitrile.

TABLE 1

| Catalyst | Hydrogenation time | % isoindoline |
| --- | --- | --- |
| Pd/C | 20 h | 1 |
| Raney Ni | 20 h | 0 |
| Rh/C | 20 h | 0 |
| Ru/C | 20 h | 0 |
| Pt/C | 6 h | 89.9 |

Reaction conditions: tetrahydrofuran, 20% by weight of catalyst, 60° C., 180 bars of hydrogen The solvent used is tetrahydrofuran, a mixture of tetrahydrofuran/water in which the water content is less than 10%, preferably less than 5%, or dimethoxyethane. In fact, it became apparent, surprisingly, that only tetrahydrofuran (used on its own or in the presence of a limited amount of water) and dimethoxyethane enabled a satisfactory conversion rate to be obtained (Table 2).

TABLE 2

| Solvent | Hydrogenation time | % isoindoline |
| --- | --- | --- |
| tetrahydrofuran | 6 h | 89.9 |
| tetrahydrofuran/water 98/2 | 6 h | 89.3 |
| dimethoxyethane | 9 h | 86.2 |
| dioxane | 20 h | 40 |

TABLE 2-continued

| Solvent | Hydrogenation time | % isoindoline |
| --- | --- | --- |
| ethanol | 20 h | 49 |
| dimethylformamide | 20 h | 0 |

Reaction conditions: catalyst Pt/C (20% by weight), 60° C., 180 bars of hydrogen The hydrogen pressure inside the reactor is from 100 to 180 bars and preferably from 150 to 180 bars.

The temperature of the reaction mixture is from 30 to 100° C. and preferably from 50 to 70° C.

The isoindoline obtained under those conditions can then readily be isolated from its reaction medium by distillation, and then purified by precipitation in the form of a hydrochloride from a solvent, such as, for example, ethanol or ethyl acetate.

The isoindoline hydrochloride so obtained has very good purity and contains, for example, less than 1.5%, preferably less than 0.2%, of 2-methylbenzylamine, which makes its use especially advantageous in the synthesis of active ingredients, such as the compound of formula (I).

By way of illustration, enantioselective reduction by catalytic hydrogenation of the isoindoline obtained according to the process of the invention enables cis-perhydroisoindole to be obtained with highly satisfactory purity and yield. That compound, when reacted with the anhydride of formula (II):

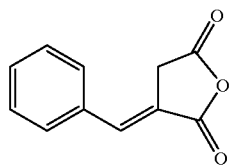

(II)

yields the compound of formula (III):

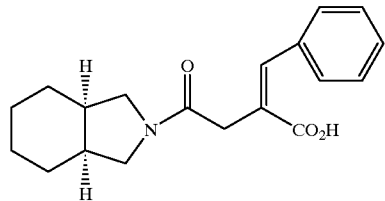

(III)

the catalytic hydrogenation of which in the presence of an asymmetric catalyst yields the compound of formula (I).

The following Examples illustrate the invention but do not limit it in any way.

The purity of the compounds was determined by gas-phase chromatography over an OPTIMA-5 amine column (Macherey-Nagel), using FID detection (flame ionisation) at 280° C.

EXAMPLE 1

Isoindoline

The reaction was carried out in an autoclave. 20 g of 5% platinum on carbon are added to 100 g of phthalonitrile dissolved in tetrahydrofuran. After purging with nitrogen, the mixture is heated at 60° C. and a hydrogen pressure of 180 bars is applied for 5 to 6 hours. After decompression and purging with nitrogen, the catalyst is removed by filtration. The tetrahydrofuran is distilled off from the filtrate at atmospheric pressure, and then isoindoline is in turn distilled off from the residue under a vacuum of 23 mbars, at a temperature of 100° C.

Isoindoline is thus obtained with a yield of 75% and purity of 89%.

EXAMPLE 2

Isoindoline hydrochloride

A solution of 2.5N hydrochloric acid in ethyl acetate is added to 69 g of isoindoline obtained in Example 1 dissolved in 458 ml of ethyl acetate. The resulting solid is recovered by filtration, washed with ethyl acetate and then dried in an oven.

Isoindoline hydrochloride is thus obtained with a yield of 82% and a purity of 98.5% with less than 1.5% of 2-methylbenzylamine.

We claim:

1. A process for the synthesis of isoindoline, wherein a solution of phthalonitrile in a solvent selected from tetrahydrofuran, a mixture of tetrahydrofuran/water, or dimethoxyethane, is subjected to a hydrogen pressure of 100 to 180 bars, at a temperature of 30 to 100° C., and in the presence of 5% Pt/C.

2. A process according to claim 1, wherein the solvent is tetrahydrofuran.

3. A process according to claim 1, wherein the solvent is a mixture of tetrahydrofuran/water in which the water content does not exceed 10%.

4. A process according to claim 3, wherein the solvent is a mixture of tetrahydrofuran/water in which the water content does not exceed 5%.

5. A process according to claim 1, wherein the solvent is dimethoxyethane.

6. A process according to claim 1, wherein the hydrogen pressure is from 150 to 180 bars.

7. A process according to claim 1, wherein the temperature is from 50 to 70° C.

8. A process according to claim 1, wherein the amount of Pt/C used is from 10 to 25% of the weight of phthalonitrile employed.

9. A process according to claim 8, wherein the amount of Pt/C used is 20% of the weight of phthalonitrile employed.

10. A process according to claim 1, wherein the amount of 2-methylbenzylamine in the isoindoline obtained does not exceed 1.5%.

11. A process according to claim 10, wherein the amount of 2-methylbenzylamine in the isoindoline obtained does not exceed 0.2%.

12. Process for the preparation of 2-(S)-benzyl-4-oxo-4-(cis-perhydroisoindol2-yl)-butyric acid wherein the intermediate isoindoline is prepared according to the process of claim 1.

* * * * *